United States Patent
Lichti et al.

(10) Patent No.: US 10,179,158 B2
(45) Date of Patent: Jan. 15, 2019

(54) COMPOSITION AND METHOD FOR CONTROL OF POST-PRANDIAL GLUCOSE

(71) Applicant: Omniblend Innovation PTY LTD, Campbellfield, Victoria (AU)

(72) Inventors: Gottfried Lichti, Essendon (AU); Christopher Walter Lichti, Essendon (AU)

(73) Assignee: Omniblend Innovation PTY LTD, Campbellfield, Victoria (AU)

(*) Notice: Subject to any disclaimer, the term of this patent is extended or adjusted under 35 U.S.C. 154(b) by 400 days.

(21) Appl. No.: 15/037,720

(22) PCT Filed: Nov. 19, 2014

(86) PCT No.: PCT/AU2014/001064
§ 371 (c)(1),
(2) Date: May 19, 2016

(87) PCT Pub. No.: WO2015/074102
PCT Pub. Date: May 28, 2015

(65) Prior Publication Data
US 2016/0296578 A1 Oct. 13, 2016

(30) Foreign Application Priority Data

Nov. 19, 2013 (AU) ................................ 2013904469

(51) Int. Cl.
| | | |
|---|---|---|
| A61K 36/00 | (2006.01) |
| A61K 36/48 | (2006.01) |
| A23L 2/52 | (2006.01) |
| A61K 9/00 | (2006.01) |
| A61K 47/36 | (2006.01) |
| A61K 47/42 | (2017.01) |
| A61K 47/46 | (2006.01) |
| A23L 33/17 | (2016.01) |
| A23L 33/21 | (2016.01) |
| A23L 33/00 | (2016.01) |
| A23L 2/66 | (2006.01) |

(52) U.S. Cl.
CPC .............. *A61K 36/48* (2013.01); *A23L 2/52* (2013.01); *A23L 2/66* (2013.01); *A23L 33/17* (2016.08); *A23L 33/21* (2016.08); *A23L 33/40* (2016.08); *A61K 9/0095* (2013.01); *A61K 47/36* (2013.01); *A61K 47/42* (2013.01); *A61K 47/46* (2013.01); *A23V 2002/00* (2013.01)

(58) Field of Classification Search
USPC ........................................................ 424/725
See application file for complete search history.

(56) References Cited

U.S. PATENT DOCUMENTS

2010/0056450 A1    3/2010   Brown et al.

FOREIGN PATENT DOCUMENTS

| WO | 99/25197 | | 5/1999 |
| WO | 99/25370 | A1 | 5/1999 |
| WO | 2007/004883 | A2 | 1/2007 |
| WO | 2009/082227 | A1 | 7/2009 |
| WO | 2010/038238 | A2 | 4/2010 |

OTHER PUBLICATIONS

International Preliminary Report on Patentability for corresponding application No. PCT/AU2014/001064 (dated Feb. 3, 2016).
International Search Report for corresponding application No. PCT/AU2014/001064 (dated Jan. 25, 2016).
Home Remedies for Diabetes: http://www.top0homeremedies.com/home-remedies/home-remedies-for-diabetes.html (Mar. 20, 2013).
Fenugreek (Methi) Benefits: http://www.speedyremedies.com/fenugreek-methi-benefits.html (Sep. 30, 2011).
Parry Enters OTC Mkt with Two Protein Drinks: http://www.business-standard.com/article/companies/parry-enters-otc-mkt-with-two-protein-drinks-111051000010_1.html (May 10, 2011).
Examination Report for corresponding EP Application No. 14864265.5, dated Jun. 6, 2017.

*Primary Examiner* — Michael V Meller
(74) *Attorney, Agent, or Firm* — LeClairRyan PLLC

(57) ABSTRACT

A drink for moderating blood glucose levels produced by a meal in a human subject suffering diabetes or IGT the drink comprising: at least one water soluble or water dispersible material selected from the group consisting of amino acids, peptides and proteins in a total amount of at least 8 g on a dry weight basis per serving of drink; aqueous liquid in an amount of from 70 ml to 400 ml per serving, and fenugreek fibre in an amount in the range of from 1 g to 15 g.

7 Claims, 4 Drawing Sheets

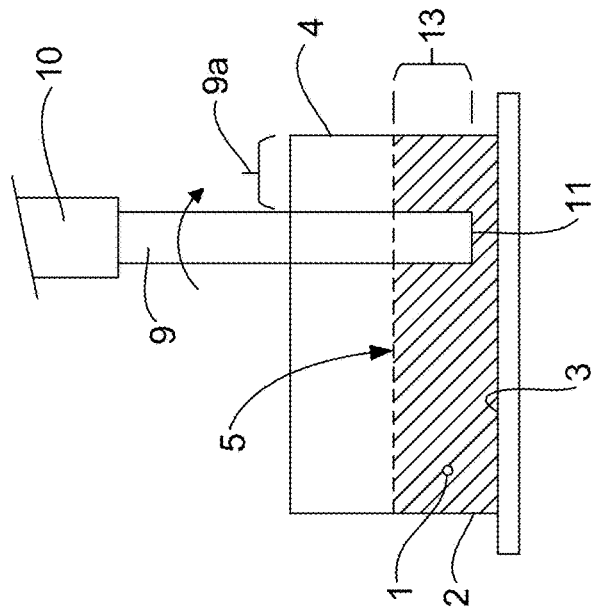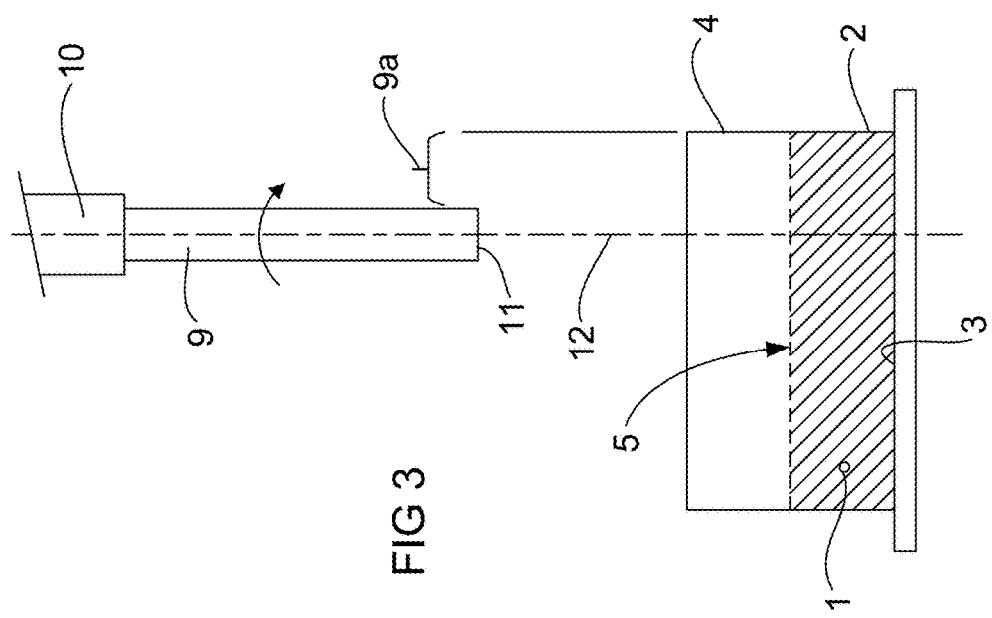

COMPOSITION AND METHOD FOR CONTROL OF POST-PRANDIAL GLUCOSE

This application is a national stage application under 35 U.S.C. § 371 of PCT Application No. PCT/AU2014/001064, filed Nov. 19, 2014, which claims the priority benefit of Australia Application No. 2013904469, filed Nov. 19, 2013.

FIELD

This invention relates to improved drink formulations for use by people with diabetes or impaired glucose tolerance (IGT) often referred to as pre-diabetes. In particular the invention relates to functional drinks that are taken in association with meals or in association with oral medications, and that moderate post-prandial glucose levels such as by reducing postprandial peak blood sugar level, or reducing postprandial blood sugar area under the curve (AUC) of blood sugar level vs. time. Embodiments also relate to a method of treatment of diabetes and IGT and a kit for use in treatment of diabetes and IGT and use of the composition for manufacture of a medicament for treatment of diabetes and IGT.

BACKGROUND

Impaired glucose tolerance (IGT) is a pre-diabetic state of dysglycemia that is associated with insulin resistance and increased risk of cardiovascular pathology. IGT may precede type 2 diabetes mellitus by many years. IGT is also a risk factor for mortality. According to the criteria of the World Health Organization and the American Diabetes Association, impaired glucose tolerance is defined as two-hour glucose levels of 140 to 199 mg per dL (7.8 to 11.0 mmol) on the 75-g oral glucose tolerance test. A patient is said to be under the condition of IGT when he/she has an intermediately raised glucose level after 2 hours, but less than would qualify for type 2 diabetes mellitus. The fasting glucose may be either normal or mildly elevated.

Diabetes includes Type 1, Type 2 and Gestational Diabetes.

Type 1 diabetes: results from the body's failure to produce insulin, and presently requires the person to inject insulin. (Also referred to as insulin-dependent diabetes mellitus, IDDM for short, and juvenile diabetes).

Type 2 diabetes: results from insulin resistance, a condition in which cells fail to use insulin properly, sometimes combined with an absolute insulin deficiency. (Formerly referred to as non-insulin-dependent diabetes mellitus, NIDDM for short, and adult-onset diabetes).

Gestational diabetes: is when pregnant women, who have never had diabetes before, have a high blood glucose level during pregnancy. It may precede development of type 2 diabetes.

Other forms of diabetes mellitus include congenital diabetes, which is due to genetic defects of insulin secretion, cystic fibrosis-related diabetes, steroid diabetes induced by high doses of glucocorticoids, and several forms of monogenic diabetes.

Both type 1 and 2 are chronic conditions that usually cannot be cured.

A number of studies have been conducted to examine the effect of diet supplements, particularly high fibre supplements on control of post-prandial glucose in healthy and diabetic subjects.

Our co-pending International Application No PCT/AU2013/000537 (Publication WO 2013/173874) describes a drink for moderating blood glucose levels produced by a meal in a human subject suffering diabetes or impaired glucose tolerance (IGT) the drink comprising:
 at least one water soluble or water dispersible material selected from the group consisting of amino acids, peptides and proteins in a total amount of at least 8 g on a dry weight basis per serving of drink;
 aqueous liquid in an amount of from 70 ml to 400 ml (preferably in an amount of from 100 ml to 250 ml and more preferably from 125 ml to 175 ml) per serving, and
wherein the drink exhibits shearbanding when subject to the shearbanding test therein described. This is referred to henceforth as centric shearbanding.

We have now found that certain aqueous compositions of water soluble or water dispersible material selected from the group consisting of amino acids, peptides and proteins and fenugreek fibre provide effective control of post-prandial blood glucose levels despite the compositions not exhibiting the standard centric shearbanding according to the standard test described in PCT/AU2013/000537.

SUMMARY

Accordingly we provide a drink for moderating blood glucose levels produced by a meal in a human subject the drink comprising:
 at least one water soluble or water dispersible material selected from the group consisting of amino acids, peptides and proteins in a total amount of at least 8 g on a dry weight basis per serving of drink;
 aqueous liquid in an amount of from 70 ml to 400 ml (preferably in an amount of from 100 ml to 250 ml and more preferably from 125 ml to 175 ml) per serving, and
fenugreek fibre in an amount in the range of from 1 g to 15 g.

It is generally preferred that the fenugreek fiber constitute at least 50% w/w, preferably at least 80% w/w of the water soluble fibre present in the composition. In one set of embodiments the composition does not exhibit centric shearbanding according to the test described in International Application PCT/AU2013/000537.

There is also provided a method for moderating the blood glucose levels produced by a meal, the method comprising:
 providing a unit serving of powder for preparation of a drink the powder comprising at least one water soluble or water dispersible material selected from the group consisting of amino acids, peptides and proteins in a total amount of at least 8 g on a dry weight basis of the powder serving and fenugreek fibre in an amount of from 1 g to 15 g; and
 mixing the unit serving of powder with aqueous liquid in an amount of from 70 to 400 grams of aqueous liquid per unit serving; and
 administering the drink prior to ingestion of the meal.

The method is particularly useful in treatment of subjects suffering diabetes (specifically type 2 diabetes) or impaired glucose tolerance.

In a further set of embodiments there is provided a kit for providing a serving of a drink for moderating blood glucose levels following a meal the kit comprising:
 at least one serving of water soluble or water dispersible material selected from the group consisting of amino acids, peptides and proteins in a total amount of at least 8 g on a dry weight basis per serving of drink;

a container having a level indicating a liquid volume of from 70 ml to 400 ml;

a closure for the container; and a space within the container above the level to allow vigorous mixing prior to consumption wherein the mixing of the powder with water filled to the level provides a drink which exhibits eccentric shearbanding on a standard rotating cylinder eccentric shearbanding test as herein described.

The kit is particularly suited to control of blood glucose levels in human subjects suffering diabetes or impaired glucose tolerance (IGT).

The composition, method and kit may not produce a drink composition which is centric shearbanding and indeed the composition is generally not centric shearbanding under the test conditions described in PCT/AU2013/000537.

However we have found that compositions which exhibit eccentric shearbanding under conditions of a eccentric shearbanding test as herein after described are useful in the control of post-prandial blood glucose, particularly in subjects suffering diabetes or IGT.

In accordance with a further embodiment there is therefore provided a drink for moderating blood glucose levels produced by a meal in a human subject suffering diabetes or impaired glucose tolerance (IGT) the drink comprising:

at least one water soluble or water dispersible material selected from the group consisting of amino acids, peptides and proteins in a total amount of at least 8 g on a dry weight basis per serving of drink;

aqueous liquid in an amount of from 70 ml to 400 ml (preferably in an amount of from 100 ml to 250 ml and more preferably from 125 ml to 175 ml) per serving, and wherein the drink exhibits eccentric shearbanding under conditions of the eccentric shearbanding test hereinafter described.

In a further set of embodiments the composition does not exhibit shearbanding under conditions of the shearbanding test described in PCT/AU2013/000537 (herein referred to as the centric shearbanding test).

DETAILED DESCRIPTION

Fenugreek

Fenugreek fibre refers to the soluble dietary fibre fraction of fenugreek (*Trigonella foenum-graecum*) seed. The amount of fenugreek fibre present in a serving of the drink composition is generally in the range of from 1 g to 15 g, preferably from 2 g to 11 g, more preferably from 3 g to 8 g, still more preferably from 4 g to 6 g.

The ratio of fenugreek fibre to said water soluble or water dispersible material (preferably protein) is preferable in a weight ratio in the range of from 2:20 to 15:20, and more preferably in the range of from 3.5:20 to 8:20.

It may be preferred that the fenugreek fibre constitute at least 50% w/w, preferably at least 80% w/w of the water soluble fibre present in the composition. In one set of embodiments the composition does not centric exhibit shearbanding according to the test described in International Application PCT/AU2013/000537.

Shearbanding

Shearbanding in a liquid driven by a rotating cylinder is characterised by the existence of (1) a band or region of high shear proximal to the rotating cylinder and (2) a band region that does not exhibit significant shear. The presence of shearbanding may be recognised in many cases by the existence of a visually apparent interface between the bands of relatively high shear and band which does not exhibit significant shear.

Centric shearbanding in a liquid is determined using a drive shaft such as a rapidly rotating cylinder in the centre of a circular container, and the presence of shearbanding may be visually observed using a dye drop spaced from the drive shaft. This is described in detail in the examples section of International Application PCT/AU2013/000537.

Eccentric shearbanding, on the other hand, is determined using a drive shaft located in an eccentric position near the wall of the container as described in the Examples section of this application.

In the presence of thickeners, fibre or the like the composition may gradually increase in viscosity if formed by mixing a dry powder composition with water. In such embodiments the determination of the presence of shearbanding is determined at 10 minutes after the commencement of vigorous mixing of the dry composition with water. This applies to both centric shearbanding and eccentric shearbanding.

In some instances, liquids may be shearbanding in an eccentric shearbanding test and non-shearbanding in a centric shearbanding test.

Protein

The water soluble or water dispersible material is preferably protein. The protein may be selected from water soluble and water dispersible protein of plant or animal origin and preferably from the group consisting casein and salts thereof and whey and hydrolysis products of whey, egg white protein or egg albumen, collagen or beef cheek collagen. Examples of water soluble or water dispersible protein of vegetable origin include soy protein, wheat protein and pea protein. Further examples of proteins include milk protein concentrate (MPC). More preferably the protein is selected from dairy whey and derivatives thereof such as hydrolysed dairy whey.

The term "peptide" means a compound that is made up of two or more amino acids joined by covalent bonds which may be formed by the elimination of molecules of water from the junction of the amino group of one amino acid and the carboxyl group of the next amino acid. The term peptide is not used to suggest a particular number of amino acids and can contain several hundred amino acids or more. "Peptide" is interchangeable with "polypeptide". Protein may be made up of a single peptide chain or a number of peptide chains joined together. The main difference between a peptide and protein is the level of structure. A protein may have primary, secondary and tertiary levels of structure.

It is preferred that the water soluble or water dispersible material selected from the group consisting of amino acids, peptides and proteins comprises one or more amino acids selected from the group consisting of lysine, threonine, leucine, isoleucine, argenine and valine.

It has been found by interrogating consumers that the regular consumption of high volumes of liquid prior to a meal can cause gastric discomfort when the meal is eaten. Preferably pre-meal drinks are no more than 300 ml in volume and more preferably no more than 200 mls.

The proportion of said water soluble or water dispersible material (preferably protein) based on total solid powder is preferably in the range 40-90% and more preferably 50-80%.

In a preferred set of embodiments, the water soluble or water dispersible material, which is preferably protein, is present in an amount of at least 10 g on a dry weight basis per serving, more preferably at least 15 g on a dry weight basis per serving. Preferred ranges for the water soluble or water dispersible material, preferably protein, are in the range of from 10 g to 40 g, more preferably 15 g to 35 g on a dry weight basis per serving of drink.

Medication

The drink is particularly suitable for treatment of a subject suffering diabetes or IGT, when the drink is used as part of the subjects IGT or diabetes management with medications. Examples of such medication include at least one selected from the group consisting of biguanides (such as metformin), enzyme inhibitors (such as angiotensin converting enzyme inhibitors (ACEI) and alpha-glucosidase inhibitors), Sulfonylureas (such as glyburide, glipizide, glimepiride, tolbutamide, chlorpropamide, acetohaxamide and tolazamide), meglitinides (such as repaglinide), thiazolidinediones (such as troglitazone, pioglitazone and rosiglitazone), dipeptidyl peptidase-4 (DPP-4) inhibitors (such as sitagliptin and salts thereof, particularly the phosphate salt) and insulin and insulin analogues (such as lispro). Examples of mixtures of medications include single compositions containing, or contemporaneous use of, biguanidas (particularly metformin) and DPP-4 inhibitors (particularly sitagliptin such as sitagliptin as the phosphate salt).

The composition may be used for subjects receiving diabetes managment therapy with combinations of drugs for treatment of a diabetes or IGT. Examples of such combination therapy include combinations of Sufonyl ureas and metformin, repaglinide and metformin, thiazolidinediones and metformin and enzyme inhibitors and metformin.

Timing

The drink may be used for administration at least once daily before a meal or before two or three meals daily.

Diabetes medications are frequently taken with a meal, and in one preferment, the drink of the invention is taken a period of time before the consumption of meal and medication. In a further set of embodiments the the medication is administered prior to taking the drink. In one embodiment the drink is consumed from 0.5 to 15 minutes before the meal and medications are consumed more than 15 minutes to one hour or from more than 15 minutes to one 30 minutes before the meal.

The drink is preferably used for administration to a subject suffering diabetes or IGT no more than 30 minutes prior to ingestion of a meal, preferably no more than 15 minutes prior to ingestion of a meal. It has been found by interrogating consumers that having a drink 15 minutes or less prior to a meal is significantly more convenient than having a drink 30 minutes prior to a meal. The composition is also particularly effective if consumed within 15 minutes before consumption of a meal.

It is particularly desirable if the drink maintains a high level of efficacy when taken at a range of times before the meal (or the meal/medication event), i.e. if the drink is effective both when taken shortly before a meal (i.e. 0.5 minutes before a meal) and when taken 15 minutes (or even longer) before a meal. This is because in practice patients are likely to use the drink at various times before a meal.

Most preferably the drink is consumed in the range of from half a minute to 15 minutes before ingestion of a meal. In the case of drink compositions prepared by mixing with an aqueous liquid it may be preferred for the drink to be consumed shortly after mixing. This is particularly the case where the drink undergoes a significant increase in viscosity after mixing.

Examples of further functional material which may be used in the composition include:

Chlorogenic acid, proposed to be responsible for the reduction in diabetes risk associated with heavy coffee intake.

Glucose uptake inhibitors, which slow the absorption of glucose and include viscosifying agents such as vegetable fibre. Specific examples include glucomannam, psyllium husk fibre, and guar gum.

Peptide analogues, such as incretin mimetics, glucagon-like analogues and agonists, amylin analogues. The main incretins are glucagon-like peptide-1 (GLP-1) and gastric inhibitory peptide (glucose-dependent insulinotropic peptide), designated GIP. GLP agonists include Exenatide, Liraglutide and Taspoglutide. A common side effect (possibly associated with decreased gastric motility) is nausea.

Protein hydrolysate, optionally with supplementation of leucine (US patent application 20090305945).

Alternative medicine and nutritional materials (not discussed above). These include:

Myrcia root extracts, commercialised as pedra hume de kaa.

Garlic, and particularly deodorised or odour-free garlic

Cinnamon (Cassia), and cinnamon bark extract

Curcurmin/turmeric

Magnesium. Recent testing has shown that magnesium (as magnesium chloride) shows promise for TYPE 2 DIABETES. Measurement of blood magnesium can establish the bioavailability of magnesium. Epedmiological studies show that high daily magnesium intake is predictive of lower TYPE 2 DIABETES in men and women.

Zinc

Coriander

Eucalyptus

Red chilli (powdered or fresh)

Green chilli (powdered or fresh)

Galangal Powder

Curry powder

Ginger

Shrimp paste

Seaweed extract

L-arabinose

Xylose

Kidney Bean Extract (food grade amylase inhibitor)

Seaweed Extract

Stevia

Juniper

Biotin

Mulberry including mulberry leaf extract

Dark chocolate (rich in flavonols)

Flavanols, a class of class of polyphenolic antioxidant that includes epichatechin.

Caiapo, which is derived from the skin of a variety of white sweet potato (*Ipomoea batas*). It is commercially available throughout Japan without prescription for treating type 2 diabetes. Several studies have been done, some concluding that HbA1c reductions are comparable with Acarbose.

Bitter melon (*Mormordica charantia*), also known as karela and bitter gourd, wild cucumber, ampalaya and cundeamor. Glucose lowering has been documented in animal models of diabetes, and antidiabetic components include charantin and vicine. Several modes of action have been proposed, including inhibition of glucose absorption in the gut, stimulation of insulin secretion, and the stimulation of hepatic glycogen synthesis.

Gurmar (*Gymnema sylvestre*). Small studies imply efficacy in type 1 diabetes and type 2 diabetes.

Prickly pear cactus (*Opuntia*, Nopal). Mainly reported in Spanish literature. Reported improved glycemic control (lower serum glucose) and improved insulin sensitivity (decreased serum insulin) following a single dose (500 g broiled or grilled nopal stems) in patients with type 2 diabetes. No effect in healthy individuals.

Coccinia indica. Double blind, placebo-controlled trial showed significant improvement in glucose tolerance.

Ginseng (e.g. Ginseng Panax). One study shows 200 mg dose decreases HbA1c by 0.5%.

Aloe vera. Tests show reduced fasting glucose in type 2 diabetes patients both in the presence and absence of concomitant sulfonylurea therapy.

Traditional Chinese Medicine has identified type 1 diabetes as "wasting and thirsting syndrome" and type 2 diabetes as "sugar urine illness". There are established treatments within TCD.

Lipoic acid (LA) also known as alpha lipoic acid (ALA),

L-Arginine, which has been classified as a "semi-essential amino acid".L-Arginine serves as a direct precursor for the biosynthesis of NO (L-Arginine is acted on by the enzyme nitric oxide synthase). The evidence appears to be positive for a role in human cardiovascular health.

Vitamin D

Coenzyme Q10. A study on patients with heart disease showed reduced plasma glucose, insulin and lipid peroxides (the latter a marker of oxidative stress). Statins (HMG-CoA reductase inhibitors, taken by many type 2 diabetes patients) can reduce serum coenzyme Q10 by up to 40%.

Polyclonal antibodies—see next section.

Polyclonal Antibodies

Yaron Ilan et al. (WO 2009113065, filed 2008) "Immunomodulating compositions for the treatment of immune-mediated disorders" describe an anti-insulin antibody for use in an oral therapy to manage symptoms of type 2 diabetes. The antibody is made from bovine colostrum.

Yaron et al. (WO 2010125565, filed 2009) "Anti-LPS enriched immunoglobulin preparation for use in treatment and/or prophylaxis of a pathologic disorder" describe the use of anti-LPS antibodies for use in an oral therapy to treat disorders associated with liver disease (this includes metabolic syndrome and type 2 diabetes).

Ching-San Lai (U.S. Pat. No. 5,747,532, filed 1995) "Combinational therapeutic methods employing nitric oxide scavengers and compositions useful therefore", teaches that the overproduction of nitric oxide (NO) is associated with a wide variety of disease states that include diabetes as well as septic shock, ischemia, ulcers, inflammatory bowel disease, arthritis, asthma, Alzheimer's disease, Parkinson's disease, multiple sclerosis, cirrhosis, encephalomyelitis, meningitis, pancreatitis, peritonitis, vasculitis, liver inflammation, renal inflammation, shock, chronic fatigue syndrome, burn infection, stroke and cancers. The invention is a method to treat overproduction of NO by using a combination of (a) an agent which inactivates species that induce NO production and (b) an agent (limited to a dithiocarbamate-containing agent) that scavenges NO. A given example of an agent in category (a) is an anti-endotoxin agent such as an antibody to endotoxin. The text of the patent discloses oral administration as a treatment option.

Particularly preferred functional materials include Vitamin D, magnesium, biotin, cinnamon, caiapo (which is derived from the skin of a variety of white sweet potato (*Ipomoea batas*)) garlic, turmeric/curcurmin and anti-lipopolysaccharide antibody.

The invention will now be described with reference to the following examples. It is to be understood that the examples are provided by way of illustration of the invention and that they are in no way limiting to the scope of the invention.

EXAMPLES

Shearbanding Test Protocol and Modified (Eccentric) Shearbanding Test Protocol

The specification and claims refer to a measure of shearbanding. The method for determining shearbanding referred to herein will now be discussed with reference to the attached drawings.

BRIEF DESCRIPTION OF THE DRAWINGS

In the drawings:

FIG. 3 is a schematic view an apparatus used to measure eccentric shearbanding in accordance with the invention showing the rotating spindle and liquid sample.

FIG. 4 is a view from above of a liquid sample prior to measurement of eccentric shearbanding with a dye mark placed 20 mm from the container wall.

In the Examples the term "WPC80" or "whey protein concentrate 80" refers to whey protein concentrate having a nominal protein content of 80% w/w of the whey protein content is in the range of from 76% w/w to 81% w/w of the whey protein concentrate.

In the Examples "WPI90" or "whey protein isolate 90" refers to whey protein isolate in which the protein concentration is nominally 90% by weight of the whey protein isolate composition. It will be understood that the concentrations may vary slightly such as from 86% to 92% w/w of the composition.

Figure 5:
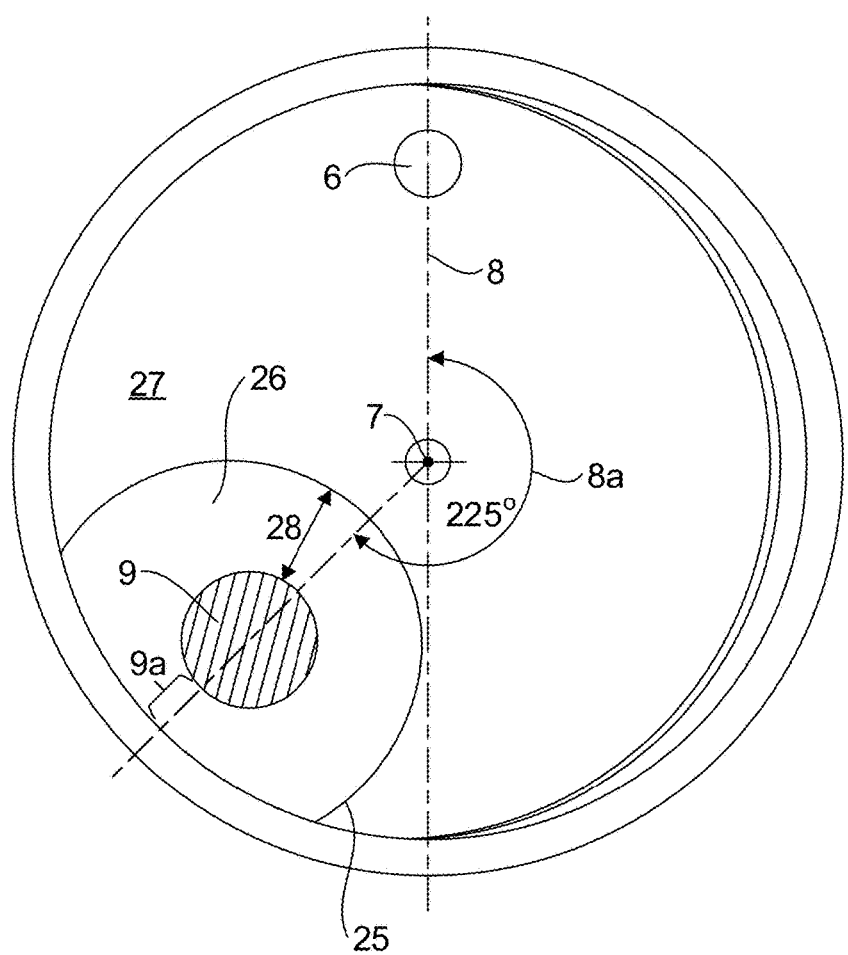
FIG. 5 is a schematic view of the apparatus of FIG. 3 during measurement of eccentric shearbanding.

Eccentric Shearbanding Protocol: Objective Measurement of Eccentric Shearbanding in a Drink Referring to FIGS. 3 to 5 a quantity of test drink (1) containing 150 mls of water (e.g. 175 total drink weight g) is well stirred and poured into a circular flat-bottomed container (2) with a base (3) and cylindrical wall (4). The container has a diameter of 90 mm and a wall (4) height of 50 mm. The height of the surface (5) drink (1) in the container (2) is 25 mm. A drop of dye (6) is placed on a reference radius (8) at a point 20 mm in from the wall (4) of the container on a notional line on the surface of the drink through the centre (7) of the circular container (4). This drop of dye (6) will be used to define angle A as described below to determine whether eccentric shearbanding is exhibited by the sample. A smooth wooden cylinder (9) of diameter 12 mm is mounted in a rotatable chuck (10) with the axis of the cylinder (9) vertical, and the flat base (11) of the cylinder (9) is located above the drink surface. The cylinder (9) is rotated at 850 rpm.

The driven-flow aspect of the measurement is initiated by lowering the rotating cylinder (9) into the drink at a distance (9a) 15 mm from the cylindrical wall (4) of the container (2) and at an angle about the centre of the container of 225° (8a) from the reference radius (8) and position of the dye marker (6). The bottom of the cylinder (11) is lowered to a depth (13) of 20 mm below the drink surface (5). After 90 seconds, the rotation of the cylinder (9) is arrested, and the cylinder (9) is slowly withdrawn from the drink.

Quantitative Definition of Eccentric Shearbanding in Terms of Angle A

Figure 6:
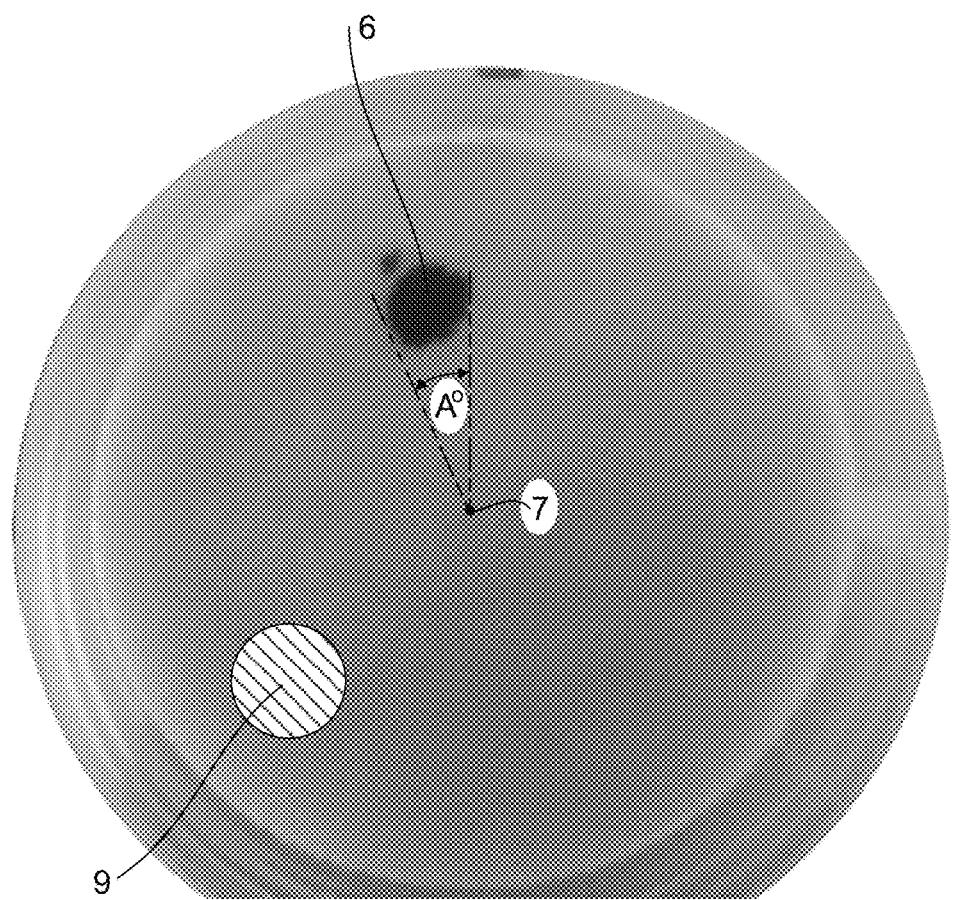
FIG. 6 is schematic view from above of a measurement of angle A° referred to in the Quantitative definition of Eccentric shearbanding.

After driving the drink (1) in the container (2) by lowering the rotating cylinder (9) for 90 seconds the dye droplet (6) is inspected. The resulting droplet may be highly elongated with a front edge and a trailing edge in which the leading edge of inner dye mark (6) has become highly elongated extending through multiple revolutions about the centre (7). Alternatively the droplet may have relatively minor elongation (so that the angle subtended at the centre of the circular container is small). The angle subtended at the centre of the circular container by the front (14) and a rear edge (15) of the drop is designated angle A (see FIG. 6). If angle A is less than 40° then the liquid is considered to exhibit shearbanding behaviour. The angle A (see FIG. 6) may be measured by protractor or other suitable angle measurement apparatus. In the case of the drink of the invention of Example 1 (FIG. 6) the angle A is determined to be 25°. In the case of the drink of Comparative Example 3 (not in accordance with the invention) the testing produces a result in which the reference dye droplet (6) is elongated through many revolutions about the rotating cylinder.

Protocol for Determination of Eccentric Shearbanding Interface Distances

The eccentric shearbanding test provides an annular band region of flow driven by the eccentric rotating cylinder. Compositions of the invention when subject to the above described eccentric shearbanding test, exhibit distinct bands or regions including an inner band or region about the rotating cylinder of relatively high shear (26) and rapid flow and an outer band (27) which does not exhibit significant shear and which is substantially static when compared with the inner high shear rapid flow region adjacent the rotating cylinder. In compositions of the invention the outer band or torroid region which does not exhibit significant shear and which is substantially static will include the dye drop and produce the eccentric shearbanding result as hereinbefore defined (that Angle A is less than 40°).

The interface between the two regions (25) can be readily determined by visual inspection while the cylinder is being driven during the test period. The distance (28) of the interface (25) from the rotating cylinder (9) can also be determined during this period using a ruler.

Eccentric Shearbanding Testing of Drinks Prepared from Mixing a Powder with Aqueous Liquid Many drinks made from reconstituted drink powder have time-variant flow characteristics. For such drinks, the following standard time sequence should be used to implement the above process. Step 1—reconstitute the drink in 150 mls of water and allow the reconstituted drink to rest for 7 minutes. Step 2—stir the rested drink and pour the drink into the above-described circular flat-bottomed container (2). After 2 minutes apply the dye drops (6) described above to the surface (5) of the drink (1), and lower the rotating cylinder (9) into the drink (1) approx. 15 mm from the container wall as described above.

The above protocol always leads to the formation of a layer of liquid that manifests local shear immediately proximal to the surface of the rotating cylinder.

In many driven drinks the shearing layer grows radially outwards from the surface of the rotating cylinder and extends throughout the liquid (although the tangential velocity of the driven drink will be significantly slower at positions further from the rotating cylinder and closer to the wall of the container). However, in drinks that exhibit eccentric shear band formation (i.e. drinks according to the current invention), a locally static layer of significant thickness (e.g. 3-20 mm or even more measured from the cylinder toward the centre of the container) develops further out from the cylinder, and this locally static outer layer coexists with the shearing inner layer. The term locally static layer means no shear or comparatively very little shear is exhibited within said layer. The simultaneous existence of an extensive shearing band and an extensive locally static band in a steady-state driven flow scenario is the characteristic feature of eccentric shear band formation.

In more general terms, eccentric shear band formation occurs in a driven-flow scenario when there is co-existence of (a) an extensive region of drink material that exhibits no local shear, and (b) an extensive region of drink material that exhibits significant local shear.

The above protocol provides a very sensitive test of eccentric\shear band formation because an extensive shearing/rotating band is always found near the surface of the rotating cylinder, and because the shape of the red dye drop is very sensitive to the existence of local shear. Eccentric shear band formation can be detected in the above protocol whenever the liquid dye drop substantially maintains its starting shape (generally circular). In the presence of even small amounts of local shear, the liquid dye drop becomes significantly elongated in response to the local shear. This liquid-drop test for local shear is significantly more sensitive than can be achieved by introducing high-contrast solid particles to the drink (as flow markers)—this is because a solid marker will move according to the resultant forces on the solid particle, and local shear can be inferred only by comparing one particle of solid marker with a separate particle of marker.

Shake-and-Take Process for Consumer Use

An elongated container may be used in preparation of drink composition for consumption by subject. Although the drink may be prepared by mixing as described in conducting the eccentric shearbanding test, we have found it to be particularly convenient for untrained consumers of the drink to prepare it by a shake-and-take method.

The shake-and-take method uses a container having a side wall and a flat bottom wall that is preferably joined to the side wall by a smooth curved transition portion to avoid recesses in which a deposit of powder may be resistant to being suspended in added water.

The container is provided with a closure which is close fitting to inhibit leakage of liquid during shaking. The container and closure may have co-operating threaded portions to provide sealing.

The container may be of volume such as 200 ml to 600 ml depending on the volume of drink which is generally no more than half the volume of the bottle.

In the shake-and-take process, a powder such as containing the protein and fenugreek is added to aqueous liquid such as water of volume such as 100 to 250 ml in the container which is generally no more than half full with the aqueous liquid.

The container closure is sealed on the container and the container is vigorously shaken. It may be shaken vertically, i.e. with the container closure facing up or down and preferably the longest axis of the container generally vertical.

However, in a further and more preferred embodiment the container is shaken with the longest dimension of the container disposed sideways and with a side-to-side motion until the powder is well suspended (generally from several seconds to 30 seconds (typically 5 to 20 seconds).

Comparative Example 1 and Example 1

Comparative Example 1

The dry ingredients of 20 g Whey Protein Concentrate (WPC-80 approximately 80% w/w whey protein) and 5 gram of guar guam were prepared. The dry powder was added to a "stock bottle" containing 150 ml of water. The lid of the stock bottle was replaced and then the bottle was shaken vigorously for 10 seconds. This drink was then put through the "eccentric shearbanding test" as described previously.

The centric shearbanding properties of the composition were determined using the procedure described in International PCT/AU2013/000537 and eccentric shearbanding properties were determined according to the procedure described above and the results are reported in Table 1 below.

Example 1

The dry ingredients of 20 g whey protein isolate (WPI-90 approximately 90% Whey Protein) and 5 gram of fenugreek seed fibre were added to a "stock bottle" containing 150 ml of water. The lid of the stock bottle was replaced and then the bottle was shaken vigorously for 10 seconds. This drink was then put through the "eccentric shearbanding test" as described previously.

The centric shearbanding properties of the composition were determined using the procedure described in International PCT/AU2013/000537 and eccentric shearbanding properties were determined according to the procedure described above and the results are reported in Table 1 below.

TABLE 1

|  | Centric Shearbanding angle A | Centric Shearbanding Y/N | Eccentric shearbanding angle A | Eccentric shearbanding Y/N |
|---|---|---|---|---|
| Fenugreek pre-meal drink | Multiple Revolutions | N | 20 deg. | Y |

|  | Shearbanding angle A | Shearbanding Y/N | Eccentric shearbanding angle A | Eccentric shearbanding Y/N |
|---|---|---|---|---|
| Guar pre-meal drink | Angle A is 25° | Y | 20 deg. | Y |
| Psyllium pre-meal drink | Multiple revolutions | N | Multiple revolutions | N |

Example 2 and Comparative Example 2

These examples compare the blood glucose response of a 60 year old Caucasian male subject previously diagnosed as pre-diabetic (i.e. having IGT) whose condition was managed by diet and exercise.

Comparative Example 2

The subject took a baseline blood glucose reading (t=−15). 12 minutes later subject took another baseline blood glucose reading (t=−3). Subject took another glucose measurement at (t=0). 10 minutes later (t=10) the subject took a blood glucose reading then consumed a meal of 4 slices of white bread (approximately 50 g of available carbohydrate) with 250 ml water over a 10 minute period. Immediately after having consumed the meal (t=15), and every 15 minutes afterwards for a further 225 minutes, subject took a blood glucose reading.

Figure 1:
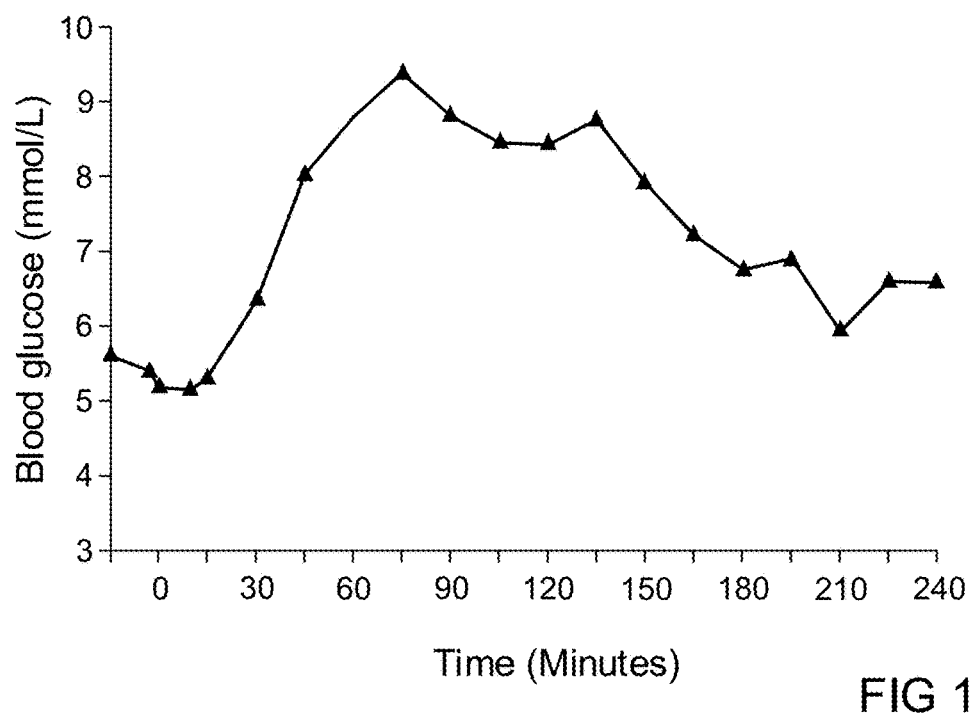
FIG. 1 is a graph of the post-prandial blood sugar measurements of a subject having ingested a control meal.

The results are shown in FIG. 1.

Example 2

The subject took a baseline blood glucose reading (t=−15). 12 minutes later subject took another baseline blood glucose reading (t=−3). Subject added the dry ingredients of 20 g Whey Protein Isolate (WPC90) and 5 g fenugreek to a "shake and take" container containing 150 ml water Subject then put the lid on the shake and take container and shook the container vigorously for 7 seconds. The subject then consumed the drink formulation as quickly as possible and took another blood glucose reading (t=0). 10 minutes later (t=10) the subject took a blood glucose reading then consumed a meal consisting of 4 slices of white bread (approximately 50 g of available carbohydrate) 10 minute period. Immediately after having consumed the meal (t=15), and every 15 minutes afterwards for a further 225 minutes, subject took a blood glucose reading. The results are shown in FIG. 2.

Conclusion

Figure 2:
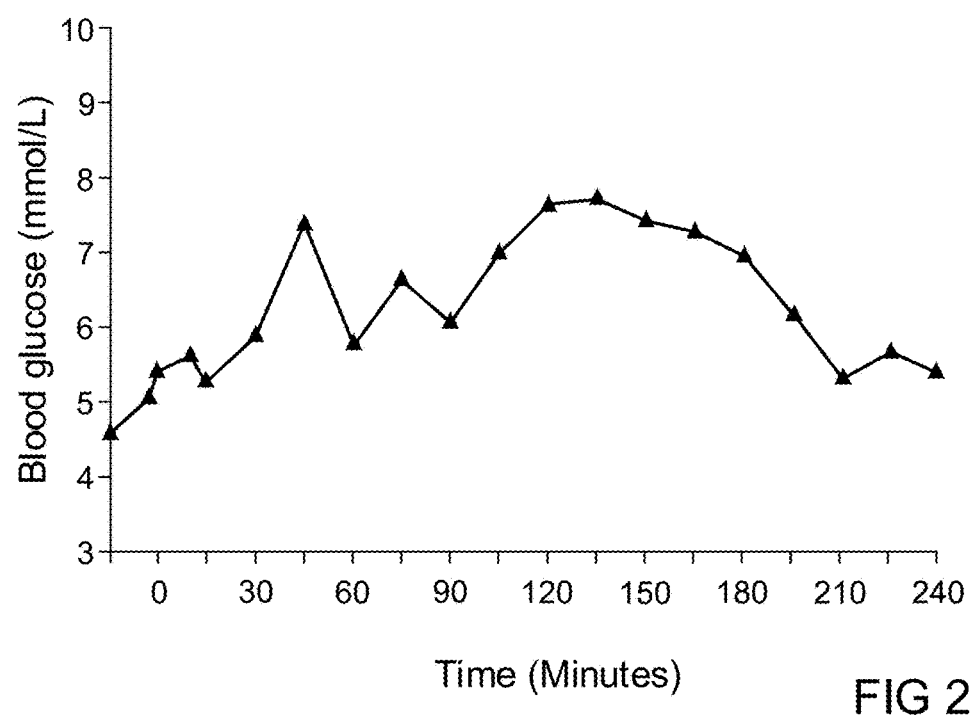
FIG. 2 is a graph of the post-prandial blood sugar measurements of a subject having ingested a drink composition of the invention about 15 minutes before the control meal.

The graphs on FIGS. 1 and 2 show the composition of the invention to provide significant moderation of the post-prandial blood glucose level in a subject who has been diagnosed as having IGT.

Our co-pending International Application No PCT/AU2012/000537 shows that diabetic and IGT subjects that consume drinks containing protein and viscosity raising fibre prior to a meal that do not have centric shearbanding qualities under the conditions of the centric shearbanding test do not perform as well as when the same subject consumed a drink that showed centric shearbanding.

Drinks that show eccentric shearbanding, as described in this patent, can lower the post-prandial blood glucose when taken prior to a meal in subjects with IGT or diabetes as effectively as when subjects with IGT or diabetes consumed drinks that showed centric shearbanding qualities prior to a meal.

Eccentric shearbanding drinks heavily out-perform drinks containing protein and viscosity raising fibre that do not show centric shearbanding or eccentric shearbanding qualities.

Examples 3 to 8

Compositions of Examples 3 to 8 were prepared by combining the drink formulation components shown in Table 2 and the eccentric shear banding properties were measured in accordance with the standard test referred to above.

The results are also reported in Table 2.

TABLE 2

| Example No. | DRINK FORMULATION | ECCENTRIC SHEARBANDING YES/NO |
|---|---|---|
| 3 | 20 g WPI (whey protein)<br>8 g Fenugreek Fibre<br>250 ml water | Yes |
| 4 | 20 g WPC80 (whey protein)<br>11.5 g Fenugreek Fibre<br>150 ml Water | Yes |
| 5 | 10 g WPC80 (whey protein)<br>5 g Fenugreek Fibre<br>150 ml water | Yes |
| 6 | 20 g WPC80 (whey protein)<br>5 g Fenugreek Fibre<br>100 ml water | Yes |
| 7 | 20 g WPI (whey protein)<br>5 g Fenugreek Fibre<br>150 ml water | yes |
| 8 | 20 g WPC80 (whey protein)<br>5 g fenugreek Fibre<br>150 ml water | yes |

The drink formulations described in Table 2 may be used to moderate blood glucose in subjects with type 2 diabetes or IGT in accordance with the invention.

The invention claimed is:

1. A method for moderating the blood glucose levels produced by a meal, in a human suffering from Impaired Glucose Tolerance (IGT) or Type 2 diabetes, the method consisting essentially of:
   providing a unit serving of powder for preparation of a drink, the powder consisting essentially of whey protein in a total amount of at least 8 g on a dry weight basis of the powder serving and soluble dietary fibre fraction of fenugreek seed in an amount of from 1 g to 15 g;
   mixing the unit serving of powder with aqueous liquid in an amount of from 70 to 400 grams of aqueous liquid per unit serving; and
   administering the drink to the human suffering from IGT or Type 2 diabetes prior to ingestion of the meal;
   wherein the drink exhibits eccentric shearbanding.

2. The method according to claim 1, wherein the weight ratio of fenugreek fibre to whey protein is in the range of from 2:20 to 15:20.

3. The method according to claim 1, wherein the drink is administered to the human suffering Type 2 diabetes or IGT within 5 minutes of commencement of mixing of the powder and aqueous liquid.

4. The method according to claim 1, wherein the drink is taken by the subject in association with oral diabetes medication comprising at least one selected from the group consisting of biguanides, enzyme inhibitors, Sulfonylureas, meglitinides, thiazolidinediones, DPP-4 inhibitors, and insulin and insulin analogues.

5. The method according to claim 1, wherein the drink is administered no more than 30 minutes prior to ingestion of the meal.

6. The method according to claim 1, wherein the whey protein is present in an amount of from 10 g to 40 g on a dry weight basis per unit serving.

7. The method according to claim 4, wherein the drink is administered 0.5-15 minutes before the meal, and medications are taken with the meal or prior to said administering the drink.

* * * * *